US00PP09373P

United States Patent [19]

Schumann

[11] Patent Number: Plant 9,373

[45] Date of Patent: Nov. 14, 1995

[54] GERANIUM PLANT NAMED FISBLIZ

[75] Inventor: Ingeborg Schumann, Albstadt, Germany

[73] Assignee: Florfis, AG, Binningen, Switzerland

[21] Appl. No.: 360,340

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fisbliz, particularly characterized by the combined features of single white flowers with purple markings, medium green leaves with zonation, vigorous growth habit, and its bushy, well branched plant habit.

1 Drawing Sheet

The present invention comprises a new and distinct cultivar of geranium, botanically known as *pelargonium peltatum* l'hert, commonly referred to as ivy geranium, and referred to by the cultivar name Fisbliz.

Fisbliz was originated from a hydridization made by inventor Ingeborg Schumann in a controlled breeding program in Galdar, Gran Canaria, Spain in 1987. The female parent was a hybrid produced from a cross between the cultivar Berliner Balkon and Salmon Queen, both characterized by their salmon pink flower color. The male parent was Amethyst, a cultivar having violet double flowers, compact plant habit, but very late flower response.

Fisbliz was discovered and selected as one flowering plant within the progeny of the stated cross by Ingeborg Schumann in 1988 in a controlled environment in Galdar, Gran Canaria, Spain.

The first act of asexual reproduction of Fisbliz was accomplished when vegetative cuttings were taken from the initial selection in Autumn 1989 in a controlled environment in Galdar, Gran Canaria, Spain, by, or under the supervision of, Ingeborg Schumann.

Horticultural examination of plants grown from these cuttings initiated in May 1990, and continuing thereafter, has demonstrated that the combination of characteristics as herein disclosed for Fisbliz are firmly fixed and are retained through successive generations of asexual reproduction.

Fisbliz has not been observed under all possible environmental conditions. The phenotype may vary significantly with variations in environment such as temperature, light intensity and daylength without, however, any variation in genotype. The following observations, measurements, and comparisions describe plants grown in Hillscheid, Federal Republic of Germany under greenhouse conditions which approximate those generally used in commercial practice.

The following traits have been repeatedly observed and are determined to be basic characteristics of Fisbliz, which in combination distinguish this geranium as a new and distinct cultivar:

1. Single white flowers with purple markings.
2. Medium green leaves with zonation.
3. Vigorous growth habit.
4. Bushy, well branched plant habit.

The accompanying color photographic drawing shows typical flower and foliage characteristics of Fisbliz, with colors being as true as possible with illustrations of this type.

In the following description, color references are made to The Royal Horticultural Society Colour Chart. The color values were determined indoors in May from plants grown indoors in Hillscheid, Federal Republic of Germany.

Classification:

*Botanical.*—A hybrid of the species *Pelargonium peltatum* l'Hert.

*Commercial.*—Ivy geranium, cv., Fisbliz

INFLORESCENCE

Umbel:

*Shape.*—Semi-spherical.
*Average diameter.*—115 mm.
*Average depth.*—55 mm.
*Peduncle length.*—165 mm.
*Peduncle color.*—Green.
*Pedicel length.*—40 mm.
*Pedicel color.*—Green, with a little anthocyanin.
*Number of flowers per umbel.*—10.

Corolla:

*Average diameter.*—47–53 mm.
*Form.*—Single, zygomorph.
*Number of petals.*—5.
*Number of petaloids.*—None.
*Color (general tonality from a distance of three meters).*—White.
*Color of upper petals.*—155D-75D.
*Color of lower petals.*—155D-75D.
*Markings, only on upper petals.*—Purple veins and a purple macula.
*Color of lower surface of petals.*—155D-75D.
*Color of sepals.*—Green.
*Number of sepals.*—5.

Bud:

*Shape.*—Narrow, elliptic.
*Color (adaxial).*—Medium green.
*Color (abaxial).*—White.

Reproductive organs:

*Androecium.*—7 Fertile anthers; orange pollen.
*Gynoecium.*—5–6 lobed stigma, pink style and stigma.

Spring flowering response period: In Hillscheid, Federal Republic of Germany, in 1993 plants had on average 1.1 flowers opened 15 weeks after planting of unrooted cuttings (pinched plants).

Outdoor flower production: The flower count in 1992 in Hillscheid, Federal Republic of Germany was between 60 and 65 flowers per plant for May through August observation period.

Durability: Shatter resistance good; rain resistance average.

PLANT

Foliage:

*Form.*—Ivy shaped.

*Margin.*—Entire.

*Color of upper surface.*—Green, approximately 137C.

*Color of zonation.*—Brown 166A.

*Tolerance of botrytis.*—Good.

General appearance and form:

*Internode length.*—5–6 mm.

*Branching pattern.*—5.0 branches per week.

*Length.*—100 cm (in September, 15-week old plants).

I claim:

1. A new distinct cultivar of geranium plant named Fisbliz, as illustrated.

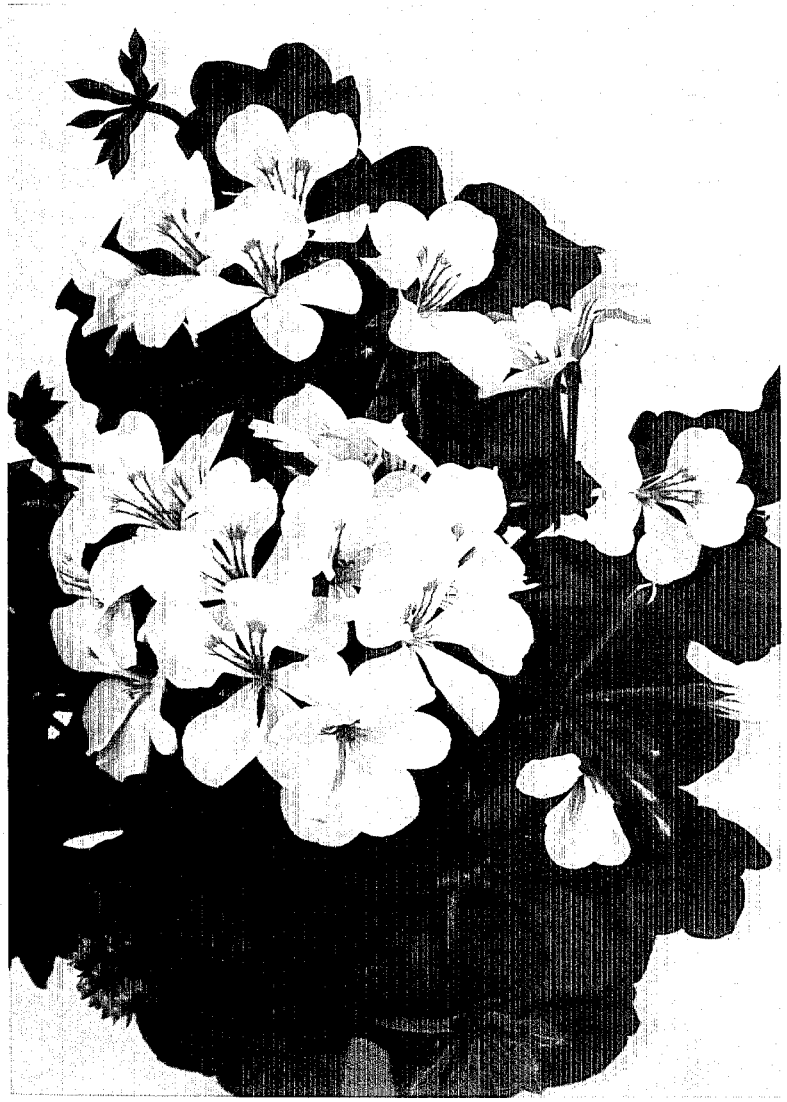

* * * * *